Figure 1:
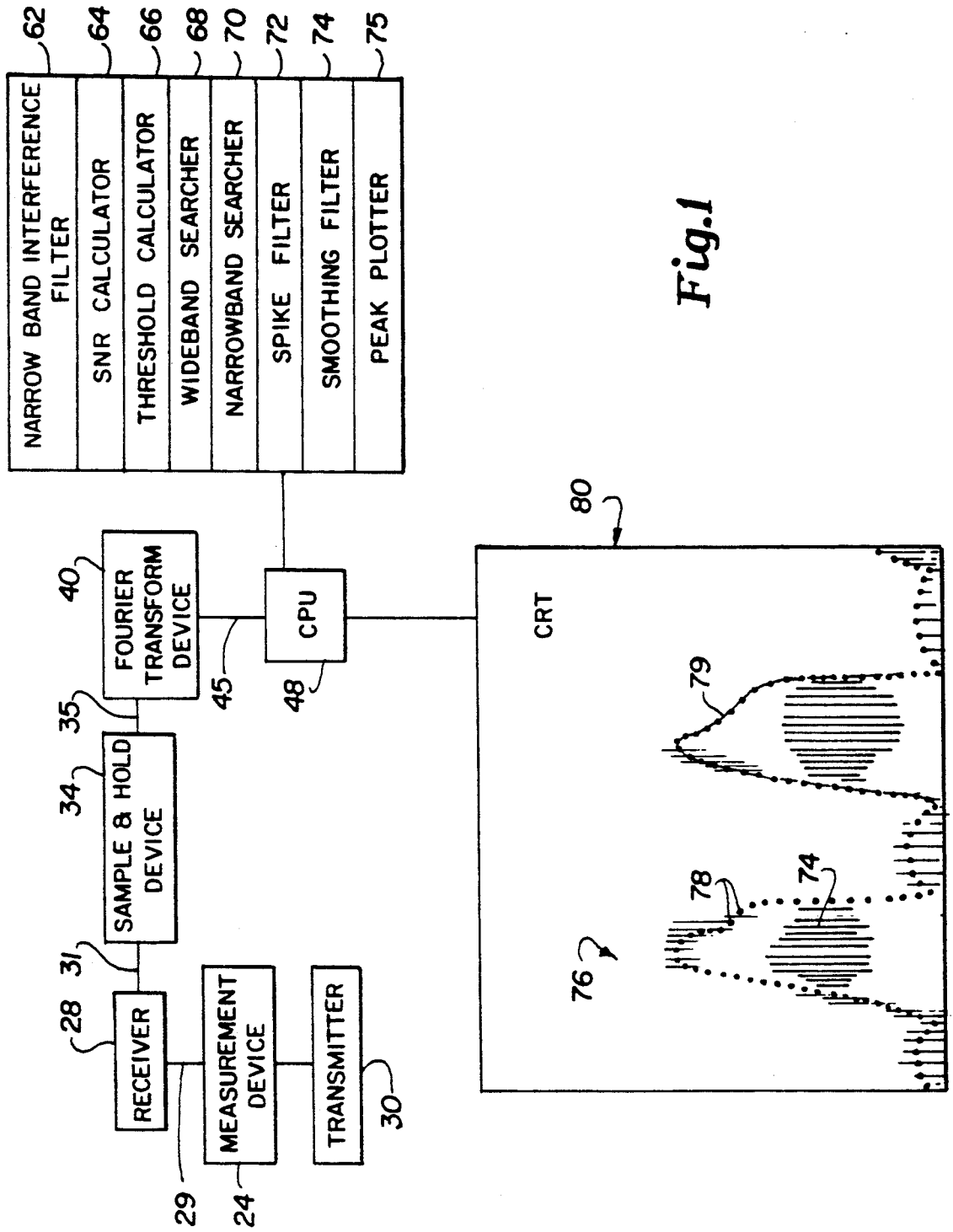

United States Patent [19]

Corl et al.

[11] Patent Number: 5,271,404
[45] Date of Patent: Dec. 21, 1993

[54] METHOD AND APPARATUS FOR PROCESSING SIGNAL DATA TO FORM AN ENVELOPE ON LINE

[75] Inventors: Paul D. Corl, Palo Alto; David Kaiser, Redwood City, both of Calif.; Ilan Lifshitz, Haifa, Israel

[73] Assignee: Cardiometrics, Inc., Mt. View, Calif.

[21] Appl. No.: 904,195

[22] Filed: Jun. 25, 1992

[51] Int. Cl.$^5$ ............................................. A61B 8/12
[52] U.S. Cl. .......................... 128/661.08; 128/662.06; 128/661.09; 73/861.25
[58] Field of Search ...................... 128/661.08, 661.09, 128/662.06, 660.07, 660.05; 73/861.25

[56] References Cited

U.S. PATENT DOCUMENTS

| | | | |
|---|---|---|---|
| 4,608,993 | 9/1986 | Albert | 73/861.25 |
| 4,848,354 | 7/1989 | Angelsen et al. | 128/660.05 |
| 5,111,823 | 5/1992 | Cohen | 128/600.07 |

OTHER PUBLICATIONS

Instruction Manual, MedaSonics, Vascular Spectrum Analyzer, Model SP25A, Version 5.0.

Service Manual, MedaSonics, Vascular Spectrum Analyzer, Model SP25A; Jul., 1986.

Primary Examiner—Kyle L. Howell
Assistant Examiner—George Manuel
Attorney, Agent, or Firm—Flehr, Hohbach, Test, Albritton & Herbert

[57] ABSTRACT

An apparatus for generating a velocity spectrogram is described. The apparatus includes a transducer which is positionable within a vessel. The transducer receives a time-varying Doppler signal which contains information related to fluid velocity values within the vessel. A Fourier transformation device processes the time-varying Doppler signal to generate a sequence of spectra. Each spectrum corresponds to a segment of the time-varying Doppler signal and defines a set of velocities and their corresponding spectral values. A device is used to identify the instantaneous spectral peak velocity within each spectra. The peak velocity corresponds to the highest velocity within a spectra which has a spectral value above a defined threshold value which is related to the background noise level. The sequence of spectral peak velocities is plotted on a visual interface device to form an instantaneous spectral peak velocity waveform.

31 Claims, 1 Drawing Sheet

METHOD AND APPARATUS FOR PROCESSING SIGNAL DATA TO FORM AN ENVELOPE ON LINE

This invention relates generally to the real time processing of time varying spectral amplitudes to form a temporal envelope of the instantaneous spectral peak frequency.

Heretofore apparatus has been provided for processing a signal to form a spectrogram which is a two dimensional gray scale display wherein the abscissa represents time, the ordinate represents frequency and the gray level at a point denotes the amplitude of the corresponding frequency component at that instant of time. To define an instantaneous spectral peak frequency envelope for a spectrogram, it has been necessary for a human being to interpret the spectrogram and to manually outline the boundary defined by the highest frequency at each instant of time which has a significant amplitude above the background noise level. This approach is time-consuming and somewhat subjective. Consequently, there is a need for a method and apparatus for defining such envelope on line and without human intervention.

Heretofore, some devices have provided computerized algorithms for determining the instantaneous spectral peak frequency envelope of a spectrogram. However, previous computerized algorithms have suffered from any of a number of problems. One problem with prior art devices is that they are too complex and therefore they are too slow to provide real time computation of the envelope. Another problem is that they are sensitive to the spectral distribution or amplitude. Another problem with prior art devices is that they are sensitive to interference signals which may be present in the spectrogram. Yet another typical problem in prior art devices is that they are sensitive to time varying noise levels.

In general, it is an object of the present invention to provide a method and apparatus which makes it possible to form an envelope of a spectrogram without human intervention.

Another object of the present invention is to provide a method and apparatus of the above character for forming an envelope which defines an instantaneous peak velocity waveform.

Another object of the present invention is to provide a method and apparatus for real time generation of a spectrogram.

Another object of the present invention is to provide a method and apparatus for eliminating interference within a spectrogram.

Additional objects and features of the invention will appear from the following description in which the preferred embodiment is set forth in conjunction with the accompanying drawing.

FIG. 1 is a block diagram of an apparatus incorporating the present invention, including a display showing a spectrogram and the envelope formed by the method of the invention.

The apparatus 20 incorporating the present invention as shown in FIG. 1 is used for processing Doppler-shifted ultrasound signals reflected by moving blood cells within a vessel so as to produce a clearly defined blood velocity spectrogram envelope. The apparatus 20 is for use with any measuring device 24 which produces a signal which varies with time, such as a guide wire having a Doppler ultrasound transducer mounted thereon for measuring blood flow velocity in a human blood vessel, such as disclosed in U.S. Pat. No. 4,967,753. Assuming that the device 24 is a Doppler ultrasound transducer, the apparatus 20 includes a transmitter 30 which supplies RF bursts at a given repetition over line 26 to the device 24 which propagates ultrasonic signals into the blood stream. A receiver 28 receives the RF signals on line 29 from the device 24 created by reflections of the propagated signals. The signals received by the receiver 28 vary in frequency and amplitude with time. Assuming the device is a Doppler ultrasound transducer, it is preferred to have the ultrasound signal from the Doppler transducer propagate in the forward direction to produce a relatively broad divergent beam that will cover a majority of the area of the vessel lumen. A 3 dB (oneway) beam width of 20 to 90 degrees is preferred. Such a broad beam, covering the majority of the vessel lumen, will ensure that the peak frequency measured in the Doppler spectrum will correspond to the highest flow velocity within the vessel forward of the ultrasonic transducer, independent of the precise orientation of the transducer.

The time-varying signal on line 31 is conveyed to a sample and hold device 34. The sampled signal from the sample/hold device 34 is supplied to a Fourier transform device 40 which is preferably a dedicated digital signal processor. A short segment of the sampled, time-varying signal on line 35 is subjected to a Fourier transformation to provide a frequency spectrum of that segment of the sampled, time-varying signal on line 35. A succession of spectra is continuously produced by subjecting subsequent short segments of the sampled, time-varying signal on line 31 to the Fourier transformation. Frequency spectra, also referred to as spectra, 42 may be generated at a suitable rate such as approximately 100 spectra/second. By way of example, a frequency spectrum comprises 256 frequency bins. Each frequency bin contains a value which represents the amplitude of the corresponding frequency component of the associated segment of the sampled, time-varying signal on line 35.

The spectrum provided by the device 40 is conveyed to CPU 48 which has associated therewith a memory 50 to process the spectral data. The CPU 48 may be a general purpose central processing unit (CPU), such as an Intel 80286. The CPU 48 operates with memory 50 and stores a set of instructions for processing the succession of spectra on line 45. The memory 50 may be a memory card, ROM, RAM, disc storage or combination thereof and stores a set of instructions which are used as hereinafter described.

The first step associated with the invention is to receive the RF signal from the measurement device 24, as previously discussed. Subsequently, spectra are generated, as previously discussed. Thereafter, each spectrum is processed in accordance with the invention, to identify the peak frequency bin which has a significant amplitude above the background noise level. The difficulty of identifying this peak frequency results from a number of factors including: the timevarying background noise level, electrical interference signals, and transient noise spikes. Furthermore, the peak frequency within each spectrum must be determined within the time required to generate the next spectrum, in order to provide an on line instantaneous peak frequency envelope.

In accordance with the invention, a number of steps are taken to identify the peak frequency The first step is to apply a narrowband interference filter 62 to the spectral data. This filter will attenuate narrowband spectral values contributed by external electronic interference signals which give rise to horizontal lines in the spectrogram display, and it will prevent the subsequent steps of the invention form tracking those horizontal interference lines. A pseudo code implementation of this filter follows:

```
Initialize Values
Threshold = Threshold_Factor * Avg_Noise
For i = 1 + Half_Bandwidth to Max_Bin -
                              Half_Bandwidth Do
If Bin(i) > Threshold AND
    Bin(i + Half_Bandwidth) < Bin(i)/Ratio AND
    Bin(i - Half_Bandwidth) < Bin(i)/Ratio
    Then
         Bin(i + 1)=Bin(i)=Bin(i-1)=Avg_Noise
```

In accordance with the pseudo code, narrowband interference is defined as a bin with spectral value greater than a threshold and bounded above and below by nearby bins with spectral values below a threshold defined relative to the spectral value of the bin under evaluation. This pattern is typical of interference generated by electronic instrumentation; it is not the pattern typical of the Doppler spectrum of flowing blood. This distinction permits the removal of external electronic interference without affecting the frequency information from the blood Doppler signal. Typical values for executing this pseudo code are: Threshold_Factor=4, Half_Bandwidth=4, Max_bin=256, and ratio=4.

To accurately identify the peak frequency, a signal-to-noise ratio is preferably calculated by SNR calculator 64. The calculation of the signal-to-noise ratio may be accomplished in the following manner. Each spectrum is processed to find a region of lowest spectral amplitude and a region of highest spectral amplitude. In the example previously cited, each spectrum consisted of 256 bins. These bins may be divided into bands (groups of bins). The value in each bin within a band may be summed with the values in the other bins within the band. The accumulated value for a band may then be compared with the values for other bands within the spectrum to find a highest value band and a lowest value band. After highest value and lowest value bands are identified for a given spectrum, these corresponding values are incorporated into the running weighted average values of highest value bands and lowest value bands to produce an average value for the maximum value band and an average value for the minimum value band. The ratio of these two values can be identified as the signal-to-noise ratio.

The following pseudo-code is suitable for determining the signal-to-noise ratio:

```
Initialize Values
Do For Each New Spectrum
    For i = min_band to max_band do
       For j = 0 to band_sum do
          temp_band = temp_band + bin(j
          +bin_count
       If temp_band > band_max
          then band_max = temp_band
       If temp_band < band_min then band_min
          =temp_band
       bin_count = bin_count + band_sum_interval
       temp_band = 0
```

-continued
```
avg_max = (1-weight) * avg_max +
              weight * band_max
avg_min = (1-weight) * avg_min +
              weight * band_min
SNR = avg_max/avg_min
```

The pseudo code provides instructions to process each spectrum. Within each spectrum, processing is done from a minimum band index (min_band) to a maximum band index (max_band). Processing can be done on all bands, but preferably a minimum band index and a maximum band index are selected to exclude bands which may contain spurious information. Thus, for instance, with 256 bins divided into 32 ascending bands of 8 bins each, min_band may be band 2, while max_band may be band 24.

Regardless of the starting point, the next step is to generate a temp_band value for a selected band or set of bands. For instance, the band_sum constant may be 32, which may correspond to 4 bands of 8 bins. The temp_band value is calculated as the signal strength for each bin(j) is accumulated. The initial bin_count index corresponds to the bin index at the beginning of the selected min_band. The bin_count index is incremented by the band_sum_interval after a band is processed. This interval is typically chosen to be smaller than the band_sum constant to enable evaluation of overlapping bandsums. For instance, a band_sum_interval may be 8, which combined with a band_sum constant of 32 means that 4 consecutive band_sums will overlap to varying degrees.

After the spectral value for each bin is added to temp_band, the value of temp_band is compared to a maximum value (band_max) and a minimum value (band_min). These values are updated if necessary, and the procedure is repeated for each band within the spectrum After a spectrum is processed in this manner, the maximum and minimum band values for the spectrum are multiplied by a weighting factor and added to avg_max and avg_min which are also multiplied by a factor which is 1 minus the previously mentioned weighting factor The results of these calculations are exponentially weighted average maximum (avg_max) and average minimum (avg_min). The weighting factor determines how many of the most recent spectra contribute significantly to the current average value. For instance, a weight factor of 1/128 may be used so that the most recent 128 spectra contribute 63% of the value of the current average. Finally, the avg_max value is divided by the avg_min value to establish a signal-to-noise ratio (SNR).

The next step associated with the invention is to determine a threshold value with threshold calculator 66. The threshold value establishes a minimum spectral value which is distinguishable from a noise value. It has been determined through empirical testing that a threshold value is successfully defined as: THRESHOLD=2* avg_min. The value avg_min is established during the signal-to-noise ratio calculation.

The next step associated with the invention is to perform a wideband search with wideband searcher 68. The wideband searcher searches each spectrum for the highest frequency set of bands containing significant spectral values. The following pseudo-code may be used for this purpose:

```
Initialize
While wide_sum > THRESHOLD and
      min_band <= bin_count and
      bin_count <= max_band do
   wide_sum = 0
   For j = 0 to wide_band do
      wide_sum = wide_sum + bin(j + bin_count)
   bin_count = bin_count + wide_band_interval
wide_location_start = bin_count - 2 *
                       wide_band_interval
wide_location_end = bin_count - 2 *
                     wide_band_interval +
                     wide_band
```

This code will search a spectrum until the accumulated spectral values for a set of bands is below the threshold value previously established. In other words, as soon as the spectral value in a set of bands is below a threshold value associated with noise, the search for a meaningful spectral value terminates and the range of the highest significant spectral value is defined. Bin_count is initialized to min_band, but to reduce processing time, bin_count may be set to an index which corresponds to a relatively strong spectral value in the positive velocity range. The wide_band constant in the pseudo-code corresponds to the number of bins which constitute a wide band. For instance, still relying upon the example of a 256 bin spectrum, a wide band search may represent 4 bands of 8 bins each, or a wide_band constant of 32.

The value wide_sum is the sum of the spectral values for the processed bins. The bin_count index is incremented by the wide_band interval after a band is processed. This interval is typically smaller than the wide_band constant to enable evaluation of overlapping wide bandsums. For instance, the wide_band_interval may be 8, which combined with a wide_band constant of 32 means that 4 consecutive wide-sums will overlap to varying degrees. The last instructions define the range of frequencies identified by the wideband search which contained viable spectral values. The instructions define this range in terms of bins. A band range may also be specified.

After the wideband search is completed by wideband searcher 68, a narrowband search is preferably performed by a narrowband searcher 70. The narrowband searcher finds a single band which contains a spectral value which is above a threshold value. The following pseudo-code may be used to find this value:

```
Initialize
narrow_threshold = threshold/band_factor
While narrow_sum > narrow_threshold and
      min_band <= bin_count and
      bin_count <= max_band do
   narrow_sum = 0
   For j = 0 to narrow_band do
      narrow_sum = narrow_sum + bin(j + bin_count)
   bin_count = bin_count +
               narrow_band_interval
narrow_location_start = bin_count -
                         narrow_band_interval
narrow_location_end = bin_count -
                       narrow_band_interval
                       + narrowband
```

This code will search a spectrum until the sum of the spectral values for a band of bins is below a threshold value. The narrow_threshold value is a modification of the previously defined threshold value. In the example above, the threshold value was calculated based upon a summation over 4 bands, thus band_factor would be equal to 4 in this example. Division of the threshold value by the band_factor results in an adjusted threshold value for the narrow band search. The narrow_band constant in the pseudo-code corresponds to the number of bins which constitute a narrow band. For instance, still relying upon the example of a 256 bin spectrum, a narrow band search may represent a band of 8 bins, or a narrow_band constant of 8. The bin_count_index is initialized to the bin number which corresponds to the start of the wideband region. The bin_count index is then incremented by the narrow_band_interval after a band is processed. This interval is typically smaller than the narrow_band constant to enable evaluation of overlapping narrow bandsums. For instance, in this context the narrow_band_interval may be 1. The value narrow_sum is the sum of the spectral values for the processed bins. The last instructions define the last narrow band range which contained significant spectral values. The instructions define this range in terms of bins. A band range may also be specified.

At the end of the narrowband search, a band is identified which represents the highest frequency band which contains a significant spectral value. The starting bin number of this frequency band can be considered to be an estimate of the instantaneous spectral peak frequency. To insure a reliable signal, preferably, this peak frequency estimate is further processed by a spike filter 72 and a smoothing filter 74. The spike filter 72 operates to eliminate spikes from the instantaneous peak frequency waveform. The spike filter uses the narrow_location_start (n_l_s) bin numbers from three consecutive spectra to filter the second of the three bin numbers, if necessary. Pseudocode for executing this function may be expressed as follows:

```
For Spectra numbered i, i+1, i+2
   set_one = abs(n_l_s(i) - n_l_s(i+1))
   set_two = abs(n_l_s(i+1) - n_l_s(i+2))
   If set_one > max_val and
      set_two > max_val and
      sign(set_one) <> sign(set_two)
   then   n_l_s(i+1) =  (n_l_s(i) +
                         n_l_s(i+2))/2
```

Three bin numbers are used to define two sets of bin number differences. The "if" clause provides a successful definition of a spike. This definition generally detects abrupt transient shifts of the peak frequency over a sequence of three successive spectra. The value for max_val may be adjusted to filter only large spikes, or it may be set to filter small spikes. If a spike is detected, then the spurious peak frequency bin number is replaced by an average of the peak frequency bin numbers of the two adjacent spectra.

After the spike filter is applied, a smoothing filter 74 is preferably applied to the previously defined narrow_location_start (n_l_s) bin numbers. The smoothing filter averages successive peak frequency bin numbers to accomplish a smoothing function. The following pseudo-code may be used for this purpose:

```
For Spectra i, i+1
   n_l_s(i+1) = (n_l_s(i) + n_l_s(i+1))/2
```

Using video techniques known in the art, each spectrum, corresponding to a selected instant in time, is plotted as a vertical column of gray-scale picture elements. The vertical position of each picture element corresponds to its frequency, and its brightness corresponds to the strength of that frequency component. A succession of spectra displayed in this format constitutes the spectrogram. The peak frequency bin (defined as $n_1_s$) of each spectrum is highlighted by a peak plotter 75 which plots a very bright dot overlying the spectrogram. Adjacent bright dots may be connected to form an envelope which represents the instantaneous spectral peak frequency waveform. As can be appreciated by one skilled in the art, the frequency shift created by the ultrasound Doppler effect can be directly translated into a blood flow velocity. Thus, as seen in the figure, the net result is a number of bright dots 78 which form an envelope 79 that traces the instantaneous spectral peak blood velocity as a function of time. This envelope 79 is superimposed over the velocity spectrogram 76.

Thus, in accordance with the invention, a method and apparatus is provided to accurately identify a spectral peak velocity. This peak velocity is not corrupted by weak noise signals which may exist at frequencies corresponding to higher velocities. In addition, a true peak velocity is identified, notwithstanding problems which may be produced by the presence of noise spikes or other irregularities within the signal.

The envelope 79 and the velocity spectrogram 76 may be projected on a cathode ray tube (CRT) 80. Each vertical line of the velocity spectrogram corresponds to a single spectrum, which in turn corresponds to a short segment of the time varying signal. The horizontal axis of the velocity spectrogram represents time, while the vertical axis represents velocity (or equivalently, frequency). Gray-scale may be used to indicate the spectral strength of each velocity component at each instant of time. Thus FIG. 1 includes a darker shading at the mid-frequencies of each spectrum.

The instantaneous spectral peak velocities for a succession of spectra are identified in the display of the velocity spectrogram 76 by a series of dots 78. Note that spectral values above the background noise level regularly appear at higher velocities than the true instantaneous spectral peak velocities attributable to blood flow. In the absence of the invention's accurate identification of the instantaneous spectral peak velocities, these spurious spectral values above the true peak velocity corrupt the peak velocity value. The velocity peak dots 78 may be connected to form an envelope 79 which identifies the true instantaneous spectral peak velocity waveform. While the velocity spectrogram 76 is literally expressed in terms of frequency, each frequency value is readily employed in a conversion to a corresponding velocity value.

One skilled in the art will recognize a number of advantages associated with the present invention. First, a velocity spectrogram is provided which preserves all relevant velocity information. The velocity spectrogram provides a robust data representation of the velocity spectrum, including the strength of each velocity component as a function of time. Second, the instantaneous spectral peak velocity waveform is determined on line, and plotted as an overlay on the velocity spectrogram. Both the velocity spectrogram and the instantaneous spectral peak velocity waveform of the present invention may be generated in real-time. Thus, as the medical professional manipulates the guidewire/Doppler device, the effect of the manipulation can be immediately observed. This instantaneous feedback permits the guidewire/Doppler device to be optimally positioned to obtain the best signal possible. Third, when used in conjunction with a broad beam Doppler ultrasound transducer, the present invention provides a position-insensitive representation of the blood flow velocity in the vessel, since the measured peak frequency of the Doppler-shifted ultrasound signal will correspond to the highest flow velocity within the vessel as long as any portion of the broad ultrasound beam is aimed in the direction of the fastest moving flow. Fourth, the real-time display of the instantaneous spectral peak velocity waveform, superimposed on top of the gray scale spectrogram display, permits the medical professional to confirm that quantitative calculations based on peak velocity waveform are accurate. The eye of the professional can easily recognize if the spectrum has a well-defined peak frequency, and furthermore, it is easily judged if the instantaneous peak velocity waveform coincides with the visible edge of the spectrogram.

We claim:

1. A method for forming a real-time representation of an instantaneous spectral peak frequency envelope of a frequency spectrogram of a measured parameter displayed on an output device, said method comprising the steps of: generating an electrical signal in the time domain with respect to a measured parameter, dividing the signal into a succession of segments and converting the segments into a corresponding succession of frequency spectra, displaying the frequency spectra as a gray scale spectrogram on an output device, finding a sequence of highest bin numbers corresponding to said succession of frequency spectra, each highest bin number corresponding to a frequency bin containing a value above a calculated threshold to substantially eliminate noise from the measured parameter data, filtering the sequence of highest bin numbers to substantially eliminate strong transient disturbances, said filtering step including the steps of removing spikes from the sequence of highest bin numbers and thereafter smoothing the sequence of highest bin numbers, highlighting the resultant sequence of highest bin numbers which represents the instantaneous spectral peak frequency envelope to distinguish the instantaneous spectral peak frequency envelope from the gray scale picture elements which form the frequency spectrogram.

2. A method as in claim 1 wherein said finding step includes filtering of narrow spectrum noise, calculating the average noise strength, calculating the signal to noise ratio, identifying said signal strength threshold, performing a wide band search to ascertain the highest frequency region with a signal strength which is greater than said signal strength threshold, conducting a narrow band search to ascertain the highest frequency region with signal strength which is greater than the narrow band signal strength threshold.

3. A method as in claim 1 wherein said highlighting step consists of interconnecting sequential highest bins to form an envelope as a function of time which is superimposed on the spectrogram.

4. A method for providing an on line envelope of a frequency spectrogram from a Doppler signal which varies with time, said method comprising the steps of receiving a Doppler signal by utilizing a Doppler ultrasound transducer with a divergent beam having a 3 dB one-way beam width of 20 to 90 degrees, generating spectra corresponding to segments of said Doppler signal, identifying a peak frequency within each of said spectra and plotting a sequence of peak frequencies to form an instantaneous spectral peak frequency envelope corresponding to an instantaneous spatial peak velocity waveform signal.

5. The method of claim 4 wherein said reading step includes the step of positioning a transducer within a vessel.

6. The method of claim 4 wherein said generating step includes the step of performing a series of Fourier transformations on said Doppler signal to produce said spectra.

7. The method of claim 4 wherein said identifying step includes the steps of defining a threshold signal value, locating a peak frequency band within each of said spectra, said peak frequency band including a set of frequency components with corresponding spectral values above said threshold, selecting a peak frequency from each of said peak frequency bands, said peak frequency representing the highest frequency component which has a spectral value above said threshold, and filtering the sequence of said peak frequency values.

8. The method of claim 4 wherein said plotting step includes presenting said peak frequency values on a presentation device and connecting said peak frequency values to adjacent peak frequency values.

9. An apparatus for generating an instantaneous spatial peak velocity waveform, said apparatus comprising a transducer positionable within a vessel containing a moving fluid, said transducer generating a transmission signal and receiving a Doppler signal corresponding to said transmission signal, said Doppler signal corresponding to velocity values of said moving fluid within said vessel, a Fourier transformation device coupled to said transducer, said Fourier transformation device executing Fourier transformations on said Doppler signal to generate velocity spectra, each of said spectra corresponding to a segment of said Doppler signal, means, coupled to said Fourier transformation device, for identifying selected velocity bins within said spectra, said selected velocity bins corresponding to the highest velocity bin within each spectrum of said spectra which contains a value which is above a defined threshold value, said identifying means including means for defining a threshold value, means for locating velocity bands with corresponding spectral values above said threshold, means for selecting said highest velocity bins containing spectral values above said threshold, and means for filtering the sequence of said highest velocity bin numbers, and means, coupled to said identifying means, for plotting said sequence of highest velocity bin numbers on a visual interface device to form an instantaneous spatial peak velocity waveform.

10. The apparatus of claim 9 wherein said Fourier transformation device is a digital signal processor.

11. The apparatus of claim 9 wherein said visual interface device is a cathode ray tube.

12. The apparatus of claim 9 wherein said plotting means includes means for presenting said spectra on said visual interface device, said sequence of highest velocity bin numbers being represented in conjunction with said spectra.

13. The apparatus of claim 9 wherein said transducer is a Doppler ultrasound transducer with a divergent beam having a 3 dB one-way beam width of 20 to 90 degrees.

14. The apparatus of claim 9 wherein said visual interface device forms said instantaneous spatial peak velocity waveform and simultaneously forms a spectrogram corresponding to said velocity values of said moving fluid so that the relationship between said spatial peak velocity waveform and said spectrogram may be assessed.

15. A method of establishing a spectral peak frequency envelope from a time-varying signal, said method comprising the steps of receiving a signal, generating a succession of frequency spectra corresponding to said signal, identifying a peak frequency bin within each spectrum of said succession of spectra to create a sequence of peak frequency bin numbers, said identifying step including the steps of defining a threshold value, locating frequency bands within said spectrum, said frequency bands including a set of frequency bins containing values above said threshold, selecting said peak frequency bin from said frequency bands, said peak frequency bin corresponding to the highest frequency which contains a value above said threshold, and plotting said sequence of said peak frequency bin numbers to form said spectral peak frequency envelope.

16. The method of claim 15 wherein said locating step includes the steps of calculating a signal-to-noise ratio for each spectrum of said succession of spectra, determining an interference threshold value based on said signal-to-noise ratio, locating, within said frequency spectrum, target bands of frequency bins at least one of which contains a value which is above said interference threshold value, and filtering said values of said target bands.

17. The method of claim 15 wherein said receiving step is performed by utilizing a Doppler ultrasound transducer with a divergent beam having a 3 dB one-way beam width of 20 to 90 degrees.

18. The method of claim 15 further comprising the step of filtering said sequence of peak frequency bin numbers.

19. An apparatus for establishing a spectral peak frequency envelope from a time-varying signal, said apparatus comprising means for receiving a signal, means for generating a succession of frequency spectra corresponding to said signal, means for identifying a peak frequency bin within each spectrum of said succession of spectra to create a sequence of peak frequency bin numbers, said identifying means including the means for defining a threshold value, means for locating frequency bands within said spectrum, said frequency bands including a set of frequency bins containing values above said threshold, means for selecting said peak frequency bin from said frequency bands, said peak frequency bin corresponding to the highest frequency which contains a value above said threshold, and means for plotting said sequence of said peak frequency bin numbers to form said spectral peak frequency envelope.

20. The apparatus of claim 19 wherein said locating means includes the means for calculating a signal-to-noise ratio for each spectrum of said succession of spectra, means for determining an interference threshold value based on said signal-to-noise ratio, means for locating, within said frequency spectrum, target bands of frequency bins at least one of which contains a value which is above said interference threshold value, and means for filtering said values of said target bands.

21. The apparatus of claim 19 wherein said receiving means is a Doppler ultrasound transducer with a divergent beam having a 3 dB one-way beam width of 20 to 90 degrees.

22. The apparatus of claim 19 further comprising the means for filtering said sequence of peak frequency bin numbers.

23. An apparatus for establishing a spectral peak frequency envelope from a time-varying signal, said apparatus comprising a Doppler ultrasound transducer, positionable within an elongated vessel, for receiving a signal, means for generating frequency spectra corresponding to said signal, means for identifying actual peak frequency bins within said spectra, said identifying means including means for defining a threshold value, means for locating, within said spectra, peak frequency bins containing values above said threshold, and means for plotting said peak frequency bins to form said spectral peak frequency envelope.

24. The apparatus of claim 23 wherein said locating means further includes means for establishing frequency bands within said frequency spectra, said frequency bands including a set of frequency bins with corresponding values above said threshold.

25. The apparatus of claim 24 wherein said locating means further includes means for selecting a peak frequency bin number from said frequency bands, each of said peak frequency bin numbers representing the highest frequency which includes a value above said threshold.

26. The apparatus of claim 23 wherein said locating means further includes means for calculating a signal-to-noise ratio for said frequency spectra, and means for determining a threshold value based on said signal-to-noise ratio.

27. The apparatus of claim 23 further comprising means for filtering said peak frequency bins.

28. Apparatus for displaying on a display device a peak frequency envelope which represents the spatial peak velocity of the blood flow in a blood vessel as a function of time at a location, comprising a guidewire having a distal extremity and having a forward looking Doppler ultrasound transducer thereon, said guidewire being adapted to be introduced into the blood vessel having blood flowing therein, first electrical means connected to the guidewire and to the transducer for causing the transducer to propagate an ultrasonic diverging beam in a forward direction into the blood flowing in the blood vessel forward of the transducer, second electrical means connected to the guidewire and to the transducer for receiving ultrasound signals reflected by the blood flowing in the blood vessel and producing a frequency spectrum which varies as a function of time as the blood flow velocity varies, means for establishing a threshold level substantially representing noise for the frequency spectrum, means for ascertaining when the values of the frequency spectrum go above and below the threshold level and generating therefrom a spectral peak velocity waveform with respect to time and means for visually displaying the spectral peak velocity waveform.

29. Apparatus as in claim 28 wherein said displaying means includes means for superimposing a grayscale spectrogram on said spectral peak velocity waveform.

30. In a method for displaying on a display device a peak frequency envelope which represents the spatial peak velocity of the blood flow in a blood vessel as a function of time at a location, by the use of a guidewire having a distal extremity and having an ultrasonic transducer mounted thereon and having first electrical means connected to the guidewire for causing the transducer to propagate an ultrasonic diverging beam in a forward direction into the blood flowing in the blood vessel and forward of the transducer and second electrical means connected to the guidewire and to the transducer for receiving ultrasonic signals reflected by the blood flowing in the blood vessel and producing a frequency spectrum which varies as a function of time as the blood flow velocity varies, comprising positioning the guidewire in the blood vessel so that the transducer is aimed in a direction substantially parallel to the blood flow, establishing a threshold level for the frequency spectrum, ascertaining when the value of the frequency spectrum goes above and below the threshold level and generating therefrom a spectral peak velocity waveform with respect to time, eliminating spurious signals from the spectral peak velocity waveform, displaying the spectral peak velocity waveform on the display device to form a peak frequency envelope in real time and observing the peak frequency envelope to ascertain the blood flow velocity in the vessel and thereafter shifting the guidewire and the transducer thereon to measure the blood flow velocity in another region of the vessel.

31. A method as in claim 30 wherein said displaying step includes superimposing a grayscale spectrogram on said spatial peak velocity waveform.

* * * * *